United States Patent [19]

Pedersen et al.

[11] 4,358,610
[45] Nov. 9, 1982

[54] PROCESS FOR THE PRODUCTION OF METHACRYLIC ACID FROM ISOBUTYRALDEHYDE

[75] Inventors: S. Erik Pedersen, Mentor; Louis F. Wagner, Solon; Christos Paparizos, Willowick, all of Ohio

[73] Assignee: The Standard Oil Company, Cleveland, Ohio

[21] Appl. No.: 239,756

[22] Filed: Mar. 2, 1981

[51] Int. Cl.$^3$ .......................................... C07C 51/235
[52] U.S. Cl. .................................... 562/535; 252/435; 252/437
[58] Field of Search ................. 562/535; 252/437, 435

[56] References Cited

U.S. PATENT DOCUMENTS 4,146,574  3/1979  Onoda et al. ..................... 423/299
4,320,227  3/1982  Matsumoto et al. ................ 562/534

FOREIGN PATENT DOCUMENTS 3001911  7/1980  Fed. Rep. of Germany .
48-78112  10/1973  Japan .
50-149611  11/1975  Japan .
51-3082715  11/1976  Japan .
53-124210  10/1978  Japan .
53-124211  10/1978  Japan .

OTHER PUBLICATIONS

Chem. Abstracts, 75:129345u (1971), (Kita et al.).
Chem. Abstracts, 77:47883v (1972), (Kita et al.).
Chem. Abstracts, 83:59769z (1975), (Ootake).

*Primary Examiner*—Nicky Chan
*Attorney, Agent, or Firm*—Gary R. Plotecher; Herbert D. Knudsen; Larry W. Evans

[57] ABSTRACT

Isobutyraldehyde is oxidized to methacrylic acid by contacting gaseous isobutyraldehyde with molecular oxygen at oxidative conditions in the presence of a catalyst of the empirical formula:

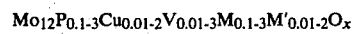

$$Mo_{12}P_{0.1-3}Cu_{0.01-2}V_{0.01-3}M_{0.1-3}M'_{0.01-2}O_x$$

where
 M is at least one of K, Rb, Cs and Tl;
 M' is at least one of Be, Mg, Ca, Sr, Ba, Nb and Sb; and
 x is a positive number that satisfies the valence requirements of the other elements present.

10 Claims, No Drawings

PROCESS FOR THE PRODUCTION OF METHACRYLIC ACID FROM ISOBUTYRALDEHYDE

BACKGROUND OF THE INVENTION

1. Field of the Invention

This invention relates to catalysis. In one aspect, the invention relates to the oxidation of isobutyraldehyde to methacrylic acid while in another aspect, the invention relates to the use of various oxide compositions as catalysts for this oxidation reaction.

2. Description of the Prior Art

The oxidation of isobutyraldehyde to methacrylic acid is known. German patent application 3,001,911 to Matsumotor et al. teaches this reaction in the vapor phase using a heteropolyacid or a mixture of a heteropolyacid and its salt as a catalyst with the general formula:

   (II)

where X is anyone of a number of different elements including copper, tin, thorium, etc, and Y (which is optional) is one of potassium, rubidium, cesium or thallium. Other teachings include Japanese Pat. No. 3,082,715, Japanese applications 78:124,210; and 75:149,611; 72:14,085, 75:12,011, 71:28,001, 78:124,211 and 48:078,112, and U.S. Pat. No. 4,146,574. While all of these teachings show the manufacture of methacrylic acid from isobutyraldehyde, some are betters than others. Indeed of the cited references, only German patent application No. 3,001,911 and Japanese patent applications 78:124,210; 75:149,611 and 78:124,211 show methacrylic acid as the dominant product and of these, only the German patent application reports as least one instance of methacrylic acid being produced in excess of 60% yield. As such, the art has room for new and more efficient processes.

SUMMARY OF THE INVENTION

According to this invention, isobutyraldehyde is oxidized to methacrylic acid by a process comprising contacting gaseous isobutyraldehyde with molecular oxygen at oxidative conditions in the presence of a catalytic amount of a composition of the empirical formula:

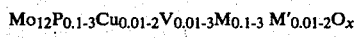

where
M is at least one of K, Rb, Cs, and Tl;
M' is at least one of Be, Mg, Ca, Sr, Ba, Nb and Sb; and
x is a positive number that satisfies the valence requirements of the other elements present.

This process is characterized by a high conversion of isobutyraldehyde to a good selectivity of methacrylic acid with relatively small amounts of carbon oxide byproducts.

DETAILED DESCRIPTION OF THE INVENTION

Catalyst:

As is evident from formula I, the catalytic composition used in this invention is at least a 7 element material, i.e. a material containing molybdenum, phosphorus, copper, vanadium, and alkali metal or thallium (M), at least one metal M', and oxygen all in designated, proportional amounts. Preferably, the subscript value of phosphorus in formula I is about 0.8 to 1.5, of copper about 0.2 to 0.8, of vanadium abot 0.2 to 0.8, of M about 1 to 3 and of M' about 0.1 to 1.5.

Preferred catalysts here used are those where M is at least one of potassium, rubidium and cesium and M' is at least one of antimony, barium and niobium. These preferred catalysts demonstrate unusually good isobutyraldehyde conversions and methacrylic acid selectivities, particularly those where M is potassium or cesium.

As is taught by formula I, certain of the components can be combinations of two or more elements, e.g. M' can be a combination of barium and niobium. In such instances, the subscript value represents the sum of the elements (e.g. for M', the sum of barium and niobium is a number within the range from about 0.01 to 2). Generally M and M' each represent but a single element.

Particularly preferred catalytic compositions here used are oxide compositions where M is potassium or cesium, M' is antimony, barium and/or niobium, and subscript value of M is at least one.

The exact structure or element arrangement of the catalysts here used are not known but the metal and phosphorus components are present in the form of their oxides, acids or oxide or oxyacid complexes. However the compositions of formula I are known not to be a mere physical mixture of their components but rather catalytic compositions were the individual components are chemically and/or physically bonded to one another.

The catalytic compositions used in this invention can be used in either the 100% active form or in a diluted form, i.e. supported or unsupported. Suitable support materials include silica, titania, alumina, zirconia, silicon carbide, boron, various phosphates, etc., with low surface area (about 1 m²/g) alumina a preferred support material. If a support is used, the catalytic composition is generally present in an amount of at least about 10 wt %, based on the combined weight of the support and the catalytic composition, and preferably in an amount of at least 30 wt %.

The catalytic compositions here used can be prepared in any one of a number of different methods, the particular method employed being a matter of convenience. Typically, the catalysts are prepared by mixing the appropriate catalyst ingredients in the proper proportions in an aqueous mixture, adjusting the pH of the mixture to about 4–7, drying the resulting aqueous slurry, and calcining the product. The ingredients can be added in any order during the preparation procedure but certain orders are preferred, particularly the mixing of the metallic ingredients prior to the addition of phosphorus (generally in the form of phosphoric acid). The ingredients employed can be the oxides, halides, nitrates, acetates or other salts of the particular metals or elements added, and particularly preferred is the use of water soluble salts of the metal components. If a support is used, the material comprising the support may be incorporated into the catalyst along with the other ingredients or the catalyst composition may be coated and/or impregnated onto or into a support core. After the catalyst ingredients have been combined to form an aqueous slurry, the slurry is taken to dryness and the dried solid obtained is heated in the presence of air, nitrogen, nitric oxide or a mixture of any two or more of these gases at a temperature sufficient to effect calcination. This calcination can take place outside the catalytic reactor or an in situ activation can be utilized. Other methods of preparation are known and broadly taught in the art.

Oxidation of Isobutyraldehyde

The compositions of formula I are highly effective catalysts for the oxidation of isobutyraldehyde to methacrylic acid. These catalytic compositions are used in the same manner as known catalysts for this reaction. The reaction generally involves the contact of gaseous isobutyraldehyde with molecular oxygen at an elevated temperature in the presence of a catalytic amount of catalyst. Exemplary of this known process is the contacting of gaseous isobutyraldehyde with molecular oxygen in the presence of steam at a temperature between about 250° C. and about 400° C., preferably between about 270° C. and about 360° C., and most preferably between about 300° C. and about 350° C. The ratio of the reactants can vary widely with molar ratio of molecular oxygen to isobutyraldehyde of about 1 to 5 being typical. The amount of steam can also vary widely from a small amount generated in the reaction to 20 or more moles of steam per mole of isobutyraldehyde. Preferably, about 1 to 10 moles of steam per mole of isobutyraldehyde is employed in the reactant feed. In certain embodiments of this invention, other gases (principally nitrogen, oxygen, carbon dioxide and carbon monoxide) can be used with or instead of steam. Molecular oxygen is most conveniently added as air.

The oxidation reaction can be conducted in almost any kind of reactor, e.g. fixed-bed, fluid-bed or transfer-line, using atmospheric, superatmospheric or subatmospheric pressure. The contact time of the reactants over the catalyst can vary from a fraction of a second to 20 or more seconds, the exact time dependent upon other reaction conditions, such as catalyst composition, feed composition, temperature, pressure, reactor design, etc.

The following examples are illustrative of certain specific embodiments of this invention. Unless otherwise indicated, all parts and percentages are by weight and the following conventions are used throughout:

IBA = isobutyraldehyde
MAA = methacrylic acid
MA = methacrolein
$VVH^{-1}$ = volume of IBA per volume of catalyst per hour.

The oxygen subscript "x" in the catalysts of the examples is defined from the atomic ratios and valences of the other elements of the catalysts.

SPECIFIC EMBODIMENTS

Catalyst Preparation

The catalysts used in the following examples were prepared by dissolving, with stirring, ammonium heptamolybdate in distilled water and heating the resulting solution to 30°–35° C. While continuously stirring the solution and maintaining its temperature, an alkali metal hydroxide and the hydroxide of M' was added. After 15 minutes aqueous solutions of copper acetate and ammonium metavanadate were sequentially added followed by 5 ml of concentrated hydrochloric acid. This mixture was then heated to 70° C. and stirred at that temperature for about 2 hours. After cooling to room temperature, phosphoric acid was added and the pH of the mixture was adjusted to about 5.6 with ammonium hydroxide. The mixture was then evaporated to dryness with stirring on a hot plate and the resulting solid was dried overnight at 110° C. The solid material was screened and the fines that went through a 50 mesh screen (U.S. Standard) were then used to coat a support. The powder was coated onto ⅛ in. Alundum ® spheres (alumina supports) so that the powder coatings (i.e. the catalysts) constituted about 35 wt % of the coated spheres. Water was used as the wetting agent in the amount of about 4% by weight of th Alundum ®.

As to those catalysts used in the comparison examples, they were prepared by essentially the same procedure except certain elements were either added or eliminated from the composition.

Process Procedure and Conditions

The reactions were conducted in a 20 cc downward-flow, fixed-bed reactor equipped with a suitcase jacket heater. All examples were performed in the same manner: After drying in a 110° C. oven overnight, first the catalysts were exposed for 2 hours at 340° C. and then for an additional hour at 370° C. to an airflow (no feed) and second, the temperature of the reactor was then decreased to about 320° C. and the catalyst exposed to the feed (charging gas). After a short stabilization period, monitoring of the reaction progress was commenced over an extended time. The off-gas effluent was measured with a soap-film meter and the off-gas composition was determined with the aid of a Carle 111 gas chromatograph. The entire scrubber liquid of each sample was diluted with distilled water to about 200 g. A weighed amount of valeric acid was used as an internal standard in a 10% aliquot of the dilute solution. A one microliter sample was then analyzed in a Hewlett-Packard Model 5710A gas chromatograph fitted with a flame ionization detector and a FF Polyester column, 60/80 mesh. The split between the various acids was determined from the gas chromatographic analysis. The process conditions and results of these experiments are reported in Table I.

TABLE I

| | | ISOBUTYRALDEHYDE OXIDATION[1] | | | | | | |
|---|---|---|---|---|---|---|---|---|
| | | Time on | Jacket | | PPC[4] to | | | |
| Example | Catalyst | Stream[2] (hrs.) | Temp.[3] (°C.) | IBA/Air/$H_2O$/$N_2$ (Moles) | MAA | MA | CO + $CO_2$ | Carbon Balance |
| 1 | $Mo_{12} P_{1.33} K_{1.5} Cu_{0.25}$ $V_{0.25} Ba_{0.1} O_x$ | 24.1 | 331 | 1/10.5/10.4/1.55 | 64.1 | 15.7 | 12 | 99.6 |
| 2 | $Mo_{12} P_{1.33} Rb_{1.5} Cu_{0.25}$ $V_{0.25} Ba_{0.1} O_x$ | 24 | 324 | 1/10.1/7.5/1.55 | 61.1 | 16.5 | 12.3 | 102.7 |
| 3 | $Mo_{12} P_{1.33} Cs_{1.5} Cu_{0.25}$ $V_{0.25} Ba_{0.1} O_x$ | 48 | 329 | 1/10.1/7.5/1.55 | 63.7 | 7.4 | 16.6 | 101.5 |
| 4 | $Mo_{12} P_{1.33} Tl_{1.5} Cu_{0.25}$ $V_{0.25} Ba_{0.1} O_x$ | 26 | 324 | 1/10.1/7.5/1.55 | 57.5 | 13.2 | 16.6 | 98.1 |
| C-1 | $Mo_{12} P_{1.33} Cu_{0.25}$ $V_{0.25} Ba_{0.1} O_x$ | 48 | 334 | 1/11.6/7.5/1.55 | 59.2 | 9.6 | 16.6 | 99.7 |

TABLE I-continued

| | | ISOBUTYRALDEHYDE OXIDATION[1] | | | PPC[4] to | | | |
| | | Time on Stream[2] (hrs.) | Jacket Temp.[3] (°C.) | IBA/Air/H$_2$O/N$_2$ (Moles) | MAA | MA | CO + CO$_2$ | Carbon Balance |
| Example | Catalyst | | | | | | | |
|---|---|---|---|---|---|---|---|---|
| C-2 | Mo$_{12}$P$_{1.33}$Na$_{1.5}$Cu$_{0.25}$V$_{0.25}$Ba$_{0.1}$O$_x$ | 45 | 333 | 1/10.1/7.5/1.55 | 49.0 | 16.5 | 20.5 | 102.6 |
| 5 | Mo$_{12}$P$_{1.33}$Cs$_{0.5}$Cu$_{0.25}$V$_{0.25}$Ba$_{0.1}$O$_x$ | 40 | 324 | 1/10.1/7.5/1.55 | 59.0 | 10.7 | 16.8 | 98.4 |
| 6 | Mo$_{12}$P$_{1.33}$Cs$_{1.0}$Cu$_{0.25}$V$_{0.25}$Ba$_{0.1}$O$_x$ | 48 | 325 | 1/10.1/7.5/1.55 | 58.4 | 10.7 | 71.1 | 98.6 |
| 7 | Mo$_{12}$P$_{1.33}$Cs$_{1.5}$Cu$_{0.25}$V$_{0.25}$Ba$_{0.1}$O$_x$ | 48 | 329 | 1/10.1/7.5/1.55 | 63.7 | 7.4 | 16.6 | 101.5 |
| 8 | Mo$_{12}$P$_{1.33}$Cs$_{2.0}$Cu$_{0.25}$V$_{0.25}$Ba$_{0.1}$O$_x$ | 43 | 324 | 1/10.1/7.5/1.55 | 62.3 | 9.6 | 14.2 | 107.6 |
| 9 | Mo$_{12}$P$_{1.33}$K$_{1.76}$Cu$_{0.25}$V$_{0.25}$Nb$_{1.76}$O$_x$ | 46 | 329 | 1/10.1/7.5/1.55 | 56.9 | 11.0 | 17.0 | 100.4 |
| 10 | Mo$_{12}$P$_{1.33}$K$_{1.5}$Cu$_{0.25}$V$_{0.25}$Sb$_{0.25}$O$_x$ | 48 | 330 | 1/10.1/7.5/1.55 | 67.4 | 9.5 | 11.8 | 103.0 |
| 11 | Mo$_{12}$P$_{1.33}$K$_{1.5}$Cu$_{0.25}$V$_{0.25}$Be$_{0.2}$O$_x$ | 44 | 329 | 1/10.1/7.5/1.55 | 61.7 | 11.4 | 15.2 | 102.3 |
| 12 | Mo$_{12}$P$_{1.33}$K$_{1.76}$Cu$_{0.25}$V$_{0.25}$Nb$_{1.76}$Ba$_{0.1}$O$_x$ | 52 | 336 | 1/8.8/7.5/1.55 | 64.6 | 12.3 | 15.7 | 100.5 |
| 13 | Mo$_{12}$P$_{1.33}$K$_{1.5}$Cu$_{0.25}$V$_{0.25}$Ca$_{0.25}$O$_x$ | 46 | 333 | 1/10.1/7.5/1.55 | 60.3 | 11.9 | 11.8 | 102.2 |

[1]For all examples and controls, atmospheric pressure was used, the conversion of IBA was essentially 100%, the VVH$^{-1}$ was about 33, and the contact time was between 2.35 and 2.40 except for Ex 1 and 12 and C-1 which were 2.28, 1.58 and 2.20 respectively.
[2]Measured from first introduction of charge gas (IBA/Air/H$_2$O/N$_2$) to extraction of sample.
[3]Actual temperature within the reactor is slightly higher due to a small reaction exotherm.
[4]Per Pass Conversion to:

$$MAA = \frac{\text{Grams of carbon as MAA}}{\text{Grams of carbon as IBA}} \times 100$$

$$MA = \frac{\text{Grams of carbon as MA}}{\text{Grams of carbon as IBA}} \times 100$$

$$CO + CO_2 = \frac{\text{Grams of carbon as CO and CO}_2}{\text{Grams of carbon as IBA}} \times 100$$

Examples 1-4 demonstrate the use of various catalysts differing only in the definition of their M component. All show good PPC to MAA with the catalysts of Examples 1 and 3 demonstrating particularly good results.

Examples C-1 and C-2 are comparative examples showing the results of a catalyst without an M component and a catalyst with sodium as the M component, respectively. As can been seen from the data, the PPC of Examples 1-4 is generally superior to that of Example C-1 and much superior to that of Example C-2. (The difference in PPC between Examples 4 and C-1 is believed attributable to the difference in temperature, a higher temperature generally favoring a higher PPC.) Moreover, although not shown by this data, catalysts containing an M component generally have a longer useful life than catalysts without an M component.

Examples 5-8 demonstrate the effect of the concentration of M component on the catalyst performance. Generally, a subscript value for M of about 1.5 is most desirable. (Example 7 and Example 3 are one and the same.)

Examples 9-13 demonstrate the use of catalysts differing only in the definition of their M' component. All show very good performance with the catalysts containing Sb and Nb/Ba showing exceptionally good performance.

EXAMPLE 14

To demonstrate the effect of temperature on the performance of the catalysts used in this invention, the procedure of Examples 1-13 and C-1 and C-2 was repeated with a catalyst of the empirical formula:

Mo$_{12}$P$_{1.33}$Cs$_{1.5}$Cu$_{0.25}$V$_{0.25}$Ba$_{0.1}$O$_x$

After the short stabilization period, the catalyst was exposed to the charging gas for a period of about 22 hours at a temperature between about 308° and 314° C. under the following conditions:

IBA/Air/H$_2$O/N$_2$ (moles)—1:10.1:7.5:1.55
VVH$^{-1}$—33.3
Pressure—atmospheric After this approximately 22 hour period, the temperature of the jacket was gradually dropped to about 270° and subsequently slowly raised in steps to a maximum temperature of about 350° C. The results are reported in Table II.

TABLE II

| EFFECT OF TEMPERATURE ON THE OXIDATION OF ISOBUTYRALDEHYDE* | | | | | | |
| Time on Stream (hrs) | Jacket Temp (°C.) | Contact Time (sec) | PPC to: | | | Carbon Balance |
| | | | MAA | MA | CO + CO$_2$ | |
|---|---|---|---|---|---|---|
| 24 | 270 | 2.64 | 15.5 | 69.4 | 6.2 | 105.0 |
| 26 | 290 | 2.55 | 38.5 | 45.2 | 8.5 | 102.2 |
| 27 | 300 | 2.50 | 53.6 | 28.2 | 10.6 | 101.6 |
| 44 | 309 | 2.46 | 61.9 | 16.4 | 12.7 | 97.9 |
| 46 | 318 | 2.42 | 63.3 | 11.1 | 14.6 | 102.9 |
| 48 | 329 | 2.38 | 63.7 | 7.4 | 16.6 | 101.5 |
| 50 | 338 | 2.34 | 59.3 | 5.5 | 20.4 | 100.7 |
| 52 | 349 | 2.30 | 54.3 | 4.3 | 23.7 | 100.4 |

*Conversion IBA = 100%; MAA and MA yields calculated as in Table I.

As the data in Table II shows, process temperatures below 300° C. favor the production of MA while process temperatures above 340° C., at least for this particular catalyst and set of conditions, are beyond the optimum. Moreover, the higher the temperature, the more waste gas (CO+CO$_2$) is produced.

Although the invention has been described in considerable detail through the preceding examples, these examples are for the purpose of illustration only and it is understood that variations and modifications can be made by one skilled in the art without departing from the spirit and scope of the invention.

What is claimed is:

1. A process for the production of methacrylic acid from the oxidation of isobutyraldehyde, the process comprising contacting gaseous isobutyraldehyde with molecular oxygen at oxidative conditions in the presence of a catalytic amount of a composition of the empirical formula:

$$Mo_{12}P_{0.1-3}Cu_{0.01-2}V_{0.01-3}M_{0.1-3}M'_{0.01-2}O_x \qquad (I)$$

where

M is at least one of K, Rb, Cs and Tl;

M' is at least one of Mg, Ca, Sr, Ba, Nb and Sb; and x is a positive number that satifies the valence requirements of the other elements present.

2. The process of claim 1 where M is K, Rb or Cs.

3. The process of claim 2 where M' is at least one of Sb, Ba and Nb.

4. The process of claim 3 where the subscript value of phosphorus in formula I is about 0.8 to 1.5, of copper about 0.2 to 0.8, of vanadium about 0.2 to 0.8, of M about 1 to 3 and of M' about 0.1 to 1.5.

5. The process of claim 4 where the composition of formula I is used with a support.

6. The process of claim 5 where the contacting is conducted at a temperature of about 250° C. to about 400° C.

7. The process of claim 5 where the contacting is conducted at a temperature of about 300° C. to about 350° C.

8. The process of claim 7 conducted in the presence of steam.

9. The process of claim 8 where the molar ratio of molecular $O_2$ to isobutyraldehyde is about 1 to 5.

10. The process of claim 9 where the support is a low surface area alumina.